United States Patent [19]

Shoesmith

[11] Plant 4,312

[45] Oct. 10, 1978

[54] CHRYSANTHEMUM NAMED WOLVERINE

[75] Inventor: Leonard H. Shoesmith, Westfield-Woking, England

[73] Assignee: Pan-American Plant Company, West Chicago, Ill.

[21] Appl. No.: 797,491

[22] Filed: May 16, 1977

[51] Int. Cl.[2] ..... A01H 5/00

[52] U.S. Cl. ..... Plt./74

[58] Field of Search ..... Plt./74

*Primary Examiner*—Robert E. Bagwill

*Attorney, Agent, or Firm*—Chas. W. Rummler

[57] ABSTRACT

A distinct chrysanthemum cultivar suitable for both year around greenhouse pot culture and for outdoor garden use as a natural season flowering plant, characterized by its single flower form with two or three rows of burnt orange ray florets surrounding a mass of yellow disc florets, the flowers being displayed in an open spray formation on strong stems and, when grown as a pot plant, being surrounded by abundant small to medium sized foliage on a relatively short and compact plant which requires no growth retardants. This plant enjoys a uniform 7-week response when flowered under photoperiod control at any time of the year.

4 Drawing Figures

BACKGROUND OF THE NEW PLANT

This chrysanthemum plant was discovered by me in 1972 as a seedling of unidentified parentage growing among random pollinated plants of the outdoor garden type in my breeding grounds at Westfield-Working, Surrey, England, and because of its apparently advantageous floral and growth characteristics, I propagated this plant at my aforesaid breeding grounds by cuttings from the original plant. My observations of the cultivar so produced indicated that the distinctive characteristics of the original plant had been retained and successive generations of the cultivar, propagated by vegetative cuttings at Westfield-Woking, Surrey, England, have demonstrated that these characteristics are firmly fixed. Also, extensive testing of this cultivar for greenhouse potted plant culture as well as for use as an outdoor garden plant has shown this plant to have commercial merit and as a result, this plant is now being propagated by vegetative cuttings and grown at West Chicago, Ill., and at Cortez, Fla., with favorable results.

DESCRIPTION OF THE DRAWINGS

This new chrysanthemum plant is illustrated by the accompanying drawings, the first of which is a full color photographic print showing a potted plant of the new variety in full bloom, the colors shown being as nearly true as it is reasonably possible to obtain by conventional photographic procedures, the photograph being of a plant propagated and grown at West Chicago, Ill., and flowered in February 1977. The second drawing is a mechanical print of a photocopy of typical leaves of the new plant taken at several stages of maturity.

DESCRIPTION OF THE NEW PLANT

The following is a detailed description of my new chrysanthemum cultivar with color designations according to the R.H.S. Colour Chart published by The Royal Horticultural Society of London, England, the stated observations having been made of plants growing at West Chicago, Ill.

THE PLANT

Origin: Seedling.

Parentage: Unidentified, this plant having been found among random pollinated plants of similar varieties.

Classification:

*Botanic.*—*Chrysanthemum morifolium.*

*Commercial.*—Greenhouse pot plant and outdoor garden chrysanthemum.

Form: Perennial herbaceous bush.

Height: 6 to 10 inches as a pot plant. 16 to 21 inches as an outdoor garden plant.

Growth: Terminal, vigorous and upright with good strength and sturdiness.

Branching: Normal under natural conditions.

Foliage: Quantity — Abundant, with four to seven leaves per 3 inches of stem.

*Leaf size.*—Length.—About 1⅜ to 3½ inches. Width — About ½ to 1⅞ inches. Shape: Lanceolate, lobed and deeply serrated. Color: Upper side — Yellow-Green 147A. Under side — Yellow-Green 147B. Surface Texture: Canescent. Venation: Pinnately veined.

*Petioles.*—About ¼ to 11/16 inch long.

THE BUD

Form: Globular.

Size:

*Diameter.*—About ¼ to 5/16 inch.

*Depth.*—About 3/16 to ⅜ inch.

Opening: The bud opens slowly.

Color:

*When phyllaries first divide.*—Yellow-Green 144A.

*When florets begin to unfurl.*—Greyed-Red 179A and 181A.

Phyllaries: Many in number, as involucral bracts borne on the outside of the receptacle.

*Form.*—Spear-shaped and upstanding.

*Color.*—Inside surface — Yellow-Green 146C. Outside surface — Yellow-Green 147B.

*Surface texture.*—Pubescent.

Peduncle: Length — About ⅜ to 1⅜ inches.

*Surface texture.*—Pubescent.

*Strength.*—Erest and strong.

*Color.*—Yellow-Green 148B.

THE FLOWER

Blooming Capability: This plant can be flowered the year around with photoperiod control.

*Response.*—7 weeks.

*Recommended flowering.*—March 1 to November 1 as a pot plant.

*Natural season flowering.*—About September 26 to October 9.

Blooms:

*Flower type.*—Composite and single.

*Size of bloom.*—Medium. Diameter — $1\frac{5}{8}$ to $2\frac{1}{2}$ inches. Depth — $\frac{3}{8}$ to $\frac{1}{2}$ inch. Shape: Flat. The shape does not change. Borne: Singly, as a head of many florets carried by a receptacle in an open spray formation.

*Florets.*—Quantity — Numerous. Form: Generally linear with an obtuse apex, the ray floret tips being predominantly spoon-shaped. Arrangement: Decorative, with the ray florets in two or three rows radiating from the disc. Texture: Medium firm. Appearance: Very slight shine. Discoloration: Considerable fade after full bloom.

| Color: | March | April | October | November |
|---|---|---|---|---|
| Outer Florets: | | | | |
| Upper side | 171A | 31A,34B 34C,170A | 24A | 171A |
| Reverse | 173A | 31B,34C 35A,35B | 167C | 171C |

*Disc forets.*—Center—144A. Perimeter—17A.

Note: Upon very close examination, it will be seen that occasionally some ray florets will show faint yellow-brown longitudinal streaks in the orange-bronze coloring.

*General color tonality of bloom.*—171B when viewed from a distance of 6 feet.

Effect of weather: This plant is not affected by hot or wet weather.

Persistence: The florets hang on and dry.

Fragrance: Typical chrysanthemum.

Lasting quality:

*On the plant.*—3 weeks.

*As cut flower.*—Not recommended for cut flower use.

REPRODUCTIVE ORGANS

Stamens: Number — 5. Arrangement — Syngenesious.

*Filaments.*—1/16 to $\frac{1}{8}$ inch long. Color: Light Yellow.

*Pollen.*—Color — Yellow.

Pistils: Number — One to each ray and disc floret.

*Styles.*—$\frac{1}{8}$ to 3/16 inch long.

*Stigmas.*—Color — Yellow.

Ovaries: Inferior bicarpellate.

This new chrysanthemum cultivar is particularly distinguished by the burnt orange coloring of the ray florets and the contrasting yellow color of the disc florets of the medium sized blooms, and by the spoon-tipped form of most, if not all, of the ray florets. The blooms are single and presented in an open spray formation with strong stems and moderate pollen production. As a potted plant, this cultivar has a uniform 7-week periodic flowering response and excellent performance as a spring, summer and fall 4 to 5 inch potted plant. The performance of this cultivar as a natural season garden chrysanthemum is also excellent. This plant has abundant foliage of small to medium sized leaves, and as a pot plant, it has a relatively short and compact plant habit which requires no growth retardants.

I claim:

1. The new and distinct chrysanthemum cultivar substantially as herein shown and described, characterized by the burnt orange and yellow coloring of its medium sized blooms which appear singly on strong stems in an open spray formation, by its uniform 7-week photoperiodic flowering response for greenhouse pot plant culture, and by its excellent performance as a spring, summer and fall potted plant and as a natural season garden chrysanthemum.

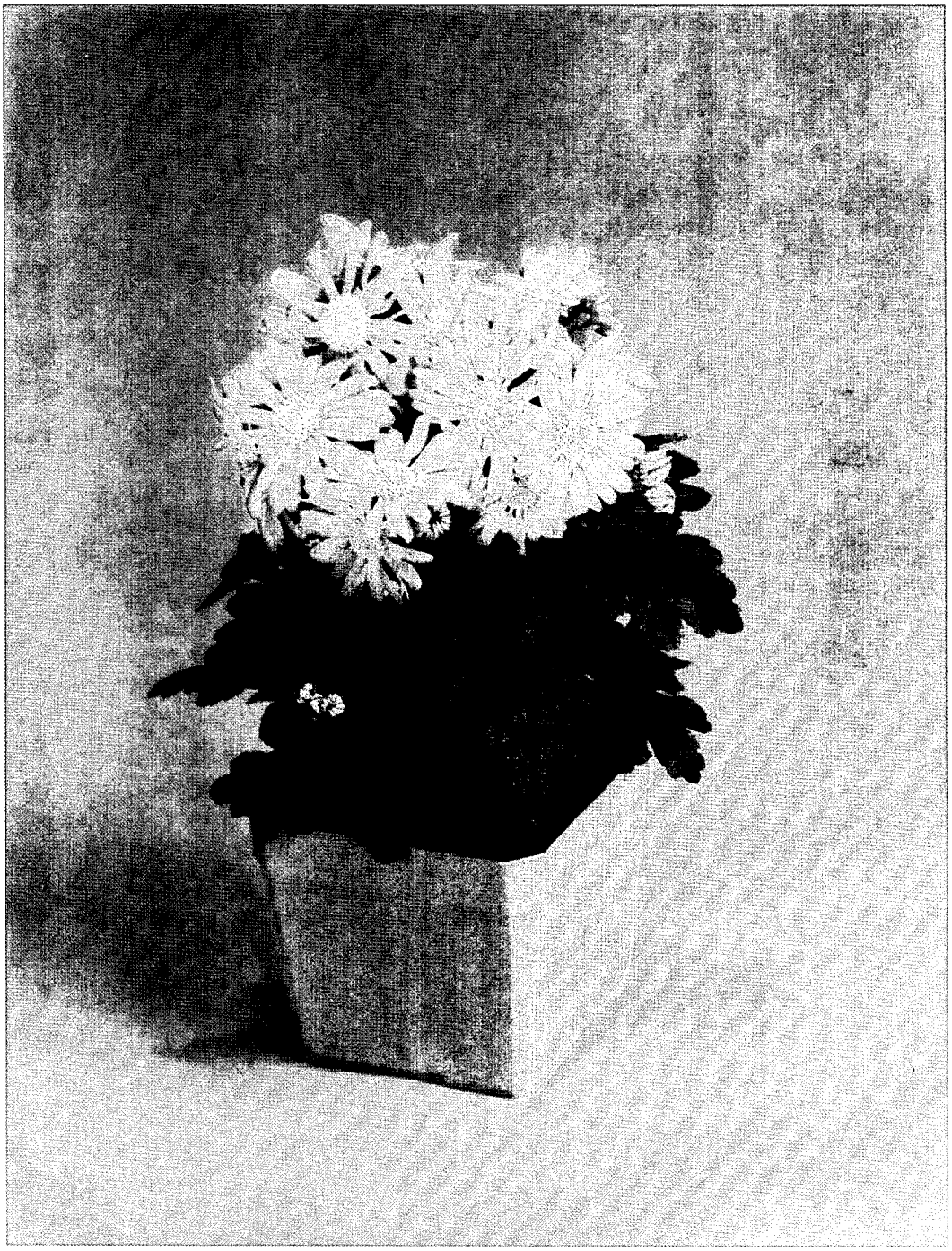

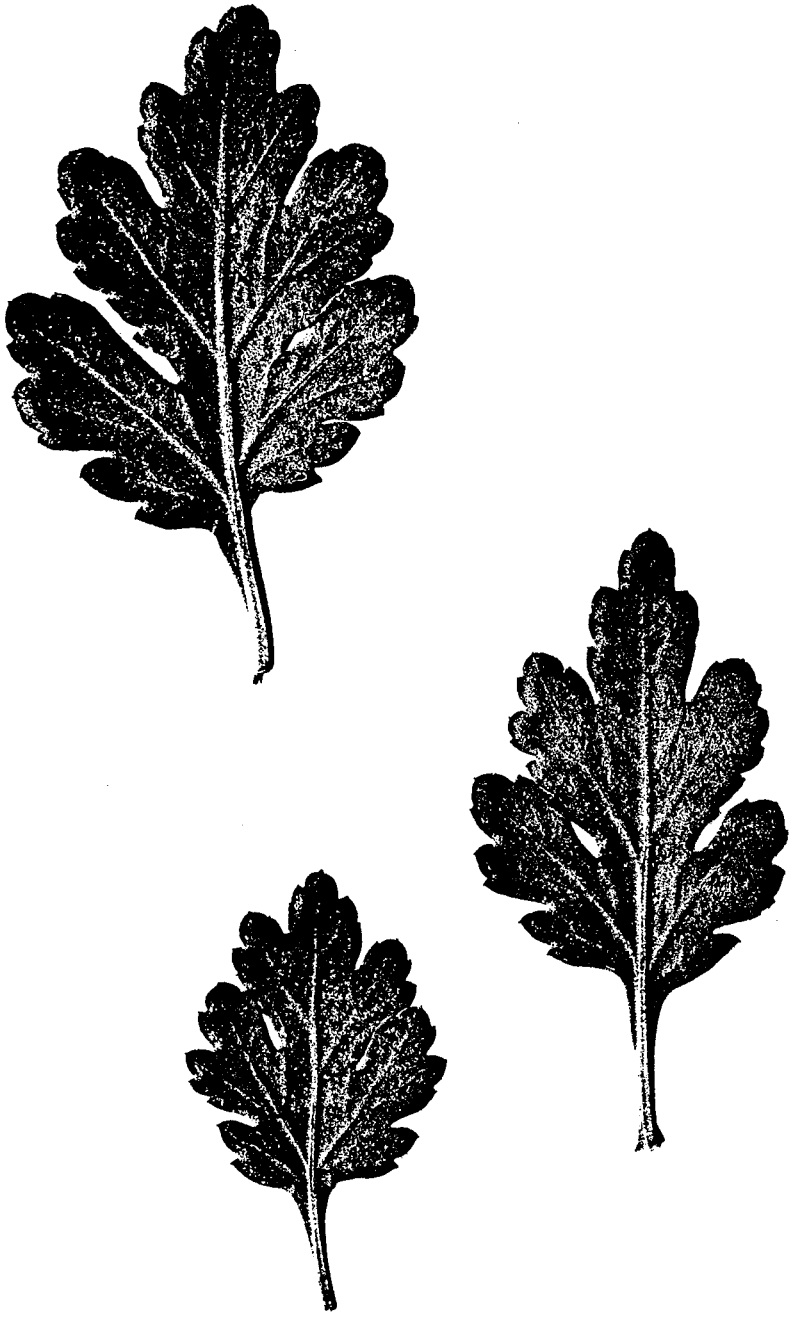

* * * * *